United States Patent [19]

Gertner

[11] Patent Number: 5,061,724

[45] Date of Patent: Oct. 29, 1991

[54] METHOD FOR TREATING ARTHRITICALLY INFLAMED BODY JOINTS, PARTICULARLY JOINTS HAVING GOUTY ARTHRITIS

[76] Inventor: Sheldon Gertner, 39 Ridge Dr., Berkeley Heights, N.J. 07922

[21] Appl. No.: 381,496

[22] Filed: Jul. 18, 1989

[51] Int. Cl.$^5$ ............... A61K 9/06; A61K 31/40; A61K 31/405

[52] U.S. Cl. .................. 514/420; 514/145; 514/415; 514/825; 514/887

[58] Field of Search ............ 424/59; 514/825, 886, 514/887, 936, 145, 415, 420

[56] References Cited

U.S. PATENT DOCUMENTS

| | | | |
|---|---|---|---|
| 3,711,606 | 1/1973 | Herschler | 514/936 |
| 4,205,089 | 5/1980 | Ladage et al. | 514/936 |
| 4,369,190 | 1/1983 | Schulte | 514/936 |
| 4,450,844 | 5/1984 | Quisno | 128/743 |
| 4,500,511 | 2/1985 | Kigasawa et al. | 514/555 |
| 4,537,776 | 8/1985 | Cooper | 514/549 |
| 4,552,872 | 11/1985 | Cooper et al. | 514/174 |
| 4,557,934 | 12/1985 | Cooper | 514/635 |
| 4,575,515 | 3/1986 | Sandborn | 514/936 |
| 4,652,557 | 3/1987 | Sandborn | 514/936 |
| 4,672,074 | 6/1987 | Harendra-Harinxma | 514/887 |
| 4,695,465 | 9/1987 | Kigasawa et al. | 514/774 |
| 4,727,064 | 2/1988 | Pitha | 514/965 |
| 4,810,496 | 3/1989 | Jensen | 514/947 |
| 4,847,283 | 7/1989 | Harendra-Harinxma | 514/887 |
| 4,871,767 | 10/1989 | Beckermann et al. | 514/936 |

Primary Examiner—Ronald W. Griffin
Attorney, Agent, or Firm—McAulay Fisher Nissen Goldberg & Kiel

[57] ABSTRACT

A method of treating inflammations of body joints in humans by topical application of anti-inflammatory agents may be used to treat joints afflicted by arthritic conditions such as gouty arthritis. The steps of the method include dissolving a predetermined quantity of a known anti-inflammatory drug, applying the medium with dissolved anti-inflammatory drug directly onto the skin covering a body joint known to be inflamed and allowing the medium with dissolved anti-inflammatory drug to be absorbed into the skin. Possible non-steroidal, anti-inflammatory drugs which may be used with the method include indomethacin, phenylbutazone and colchicine. Steroidal non-inflammatory drugs may also be used.

5 Claims, No Drawings

1

METHOD FOR TREATING ARTHRITICALLY INFLAMED BODY JOINTS, PARTICULARLY JOINTS HAVING GOUTY ARTHRITIS

FIELD OF THE INVENTION

The present invention relates to a method for treating inflammations of body joints in humans, and in particular, joints afflicted by arthritic conditions such as gouty arthritis.

BACKGROUND OF THE PRESENT INVENTION

The chronic treatment of gout affecting the big toe or other toes requires daily or prophylactic treatment with one or more drugs. These drugs, such as colchicine, allopurinol, probenecid or indomethacin or combinations of these, have numerous side effects that can cause with time considerable toxicity. In addition, they may adversely affect the action of other drugs given to the patient to treat completely different conditions. More importantly, when the drugs are used to affect small areas such as the toes, relatively high doses must be given which produce overall much greater effects on other body tissues than the toes due to the general distribution of the drug when given by the oral route.

It would appear more logical, when the object of therapy is to produce a local anti-inflammatory effect, to treat each local site of inflammation with lower doses of the anti-inflammatory drugs than would be given orally. The local concentrations under these conditions, at the joint, would still be considerably higher than giving such anti-inflammatory drugs orally, where the drug is distributed to all the body tissues and thus diluted. This local application should be domethacin and phenylbutazone (non-steroidal anti-inflammatory agents) as well as colchicine, which works by a different mechanism.

It is an object of the present invention, therefore, to provide anti-inflammatory treatment of joints by topical application so as to avoid the need for high concentrations of anti-inflammatory drugs normally taken orally and to enable a therapeutic effect to be provided to the joint by more direct and therefore less toxic application.

SUMMARY OF THE INVENTION

In accordance with the invention, a method of treating inflammations of body joints in humans by topical application of anti-inflammatory agents comprises the steps of dissolving a predetermined quantity of a known anti-inflammatory drug in a medium capable of being absorbed into the skin, applying the medium with dissolved anti-inflammatory drug directly onto the skin covering a body joint known to be inflamed and allowing the medium with dissolved anti-inflammatory drug to be absorbed into the skin and joint.

DESCRIPTION OF THE PREFERRED EMBODIMENTS

Since the inventor himself suffers periodically from acute attacks of gout and often has inflammation of the big toe during the chronic phase as seen by a red band covering the mid joint of the large toe (which is not as excruciatingly painful as during the acute attack, but nevertheless feels abnormal and prevents normal movement of toe), the inventor decided to attempt treatment of the big toe by direct topical application, i.e., a crude trans-dermal preparation.

While it is known that getting drugs through the skin requires considerable technology, which generally is available today as specially devised (trans-dermal patches) placed on the skin or iontophoresis, such techniques were not available to the inventor. The inventor did, however, prepare a type of trans-dermal patch in order to pass indomethacin locally through the skin and, presumably, to achieve higher concentration at the joint of the big toe.

An ordinary adhesive bandage, i.e., a BAND-AID ® adhesive strip (one inch across) was utilized and a small layer of hand cream containing aloe vera was placed on the pad of the bandage strip. It is noted that this type of cream easily penetrates and is absorbed into the skin within about 30 minutes. Assuming that an anti-inflammatory drug were dissolved in the cream, then, when the cream was absorbed, so would be the drug. About 4 mg of powder of indomethacin was sprinkled on top of the layer of cream on the pad of the strip. An additional small amount of hand cream was placed on top of the powder and the drug was gently dissolved into the cream with the finger. The bandage was then adhered on the inflamed area of the big toe. This technique was done on retiring at night as well as in the morning (twice a day). A rough estimate of $0.75$ mg/cm$^2$ was the concentration employed. It should be noted that a typical capsule of indomethacin for oral consumption contains 25 mg. Such 25 mg capsule is normally prescribed to be taken at least three times a day during chronic phase of gout and in double the dosage during an acute attack.

The technique has been repeated at least 45 times and has resulted in considerable improvement to the affected area for about 10 hours. Just applying a placebo of cream without the drug has not given equivalent results. Not only has the redness of the affected area paled or in some cases disappeared, but the stiffness of the joint as well has disappeared. The bandage, when removed eight hours after application, has shown only small traces of the hand cream. Thus, the presumption of absorption of the drug through the skin seems justified and presumably at the joint, which is so close to the skin at that site.

By utilizing one of the newer modes of trans-dermal applicators more controlled and better absorption should take place than the experiment referred to above. In addition, such applicators, would provide a more controlled site for delivery. Various types of trans-dermal delivery systems would be appropriate in delivering the anti-inflammatory drug to the skin and joint in accordance with the invention. Two such approaches are disclosed, for example, in U.S. Pat. No. 4,450,844 and U.S. Pat. No. 4,336,243, which disclosures are incorporated herein by reference.

It is believed that the local patch approach holds out the possibility of treating small, locally inflamed areas of the body very effectively, such as the toes or other joints. Not only will the anti-inflammatory drug be given at the site where it is needed in the highest concentration to produce its therapeutic action, but the total dose of drug to the patient will be reduced by a minimum of six fold and possibly more. The inherent toxicity of these particular drugs, when given chronically, will be considerably reduced, thus resulting in much less morbidity.

Drugs that could be used by this methodology to treat gout would be non-steroidal, anti-inflammatory agents, steroids and colchicine and any other drugs that would reduce inflammation at the site. In addition, drugs of this type, other than colchicine, which is specific only for gout, could be used to treat other arthridites. Using the data obtained to date, it would appear that a concentration of 0.75 mg of indomethacin per square cm ±10 fold is an effective therapeutic range.

While no tests have yet been made using other anti-inflammatory drugs or an anti-inflammatory drug topically on a larger joint such as an elbow or knee, there is no reason to believe that the same relief would not be obtained for similar treatment although a higher concentration of the drug may be necessary. While the application has been described using skin cream as a skin-absorbing medium for the dissolved anti-inflammatory agent, other media absorbable by the skin may be employed. In this regard, various creams, oils or gels may be employed to provide slow, but effective, skin absorption.

Further, while the example described above refers to application of a patch bearing the medium with dissolved agent to the joint, the medium (with dissolved agent) may also be applied directly to the skin at the inflamed joint.

While the foregoing description represents the preferred embodiments of the present invention, it will be obvious to those skilled in the art that various changes and modifications may be made therein without departing from the true spirit and scope of the present invention.

What is claimed is:

1. A method for alleviating the symptoms of gouty arthritis in an afflicted joint of a human comprising applying to the skin area nearest the afflicted joint a composition consisting essentially of a mixture of a skin cream capable of being absorbed into the skin and a gouty arthritis symptom alleviating effective amount of indomethacin and allowing said mixture to remain in contact with the skin for a time period sufficient to alleviate the gouty arthritis symptom.

2. The method of claim 1 wherein the mixture is placed on a bandage and the bandage is secured to the skin area.

3. The method of claim 2 wherein the bandage is allowed to remain in contact with the skin area for at least 30 minutes.

4. The method of claim 3 wherein the skin cream contains aloe vera.

5. The method of claim 4 wherein the symptom alleviating effective amount of indomethacin is 0.75 $mg/cm^2 \pm 10$-fold based on the skin area.

* * * * *